United States Patent [19]

Layton

[11] 4,219,026
[45] Aug. 26, 1980

[54] BLADDER HEMOSTATIC CATHETER

[75] Inventor: Terry N. Layton, Arlington Heights, Ill.

[73] Assignee: The Kendall Company, Boston, Mass.

[21] Appl. No.: 942,523

[22] Filed: Sep. 15, 1978

[51] Int. Cl.³ .......................................... A61M 25/00
[52] U.S. Cl. .................... 128/325; 128/344; 128/349 B
[58] Field of Search ......... 128/246, 325, 344, 348–351

[56] References Cited

U.S. PATENT DOCUMENTS

| | | | |
|---|---|---|---|
| 1,089,805 | 3/1914 | Wolf | 128/349 R |
| 1,922,084 | 8/1933 | Gerow | 128/349 B |
| 2,849,001 | 8/1958 | Oddo | 128/325 |
| 3,516,407 | 6/1970 | Ruggero | 128/325 |
| 3,572,375 | 3/1971 | Rosenberg | 128/274 X |
| 4,022,216 | 5/1977 | Stevens | 128/349 B |

OTHER PUBLICATIONS

ACMI Catalogue–1952, p. 190, 128–325.

*Primary Examiner*—Dalton L. Truluck
*Attorney, Agent, or Firm*—Powell L. Sprunger

[57] ABSTRACT

A bladder hemostatic catheter comprising, an elongated shaft having a lumen extending along the shaft, a tip at the distal end of the shaft, and an opening adjacent the distal end of the shaft communicating between the lumen and the outside of the shaft. The catheter has an inflatable balloon of elastic material covering a distal end section of the shaft, with the balloon having a proximal portion secured circumferentially around the shaft, and with the balloon defining a cavity intermediate the balloon and the shaft communicating with the opening. The balloon is capable of receiving 600 to 1000 cubic centimeters of fluid and assuming a generally spherical shape in an inflated state of the balloon. The catheter has valve means to permit passage of fluid from a source of fluid to the lumen while preventing passage of fluid from the lumen during inflation of the balloon.

1 Claim, 4 Drawing Figures

U.S. Patent      Aug. 26, 1980      4,219,026
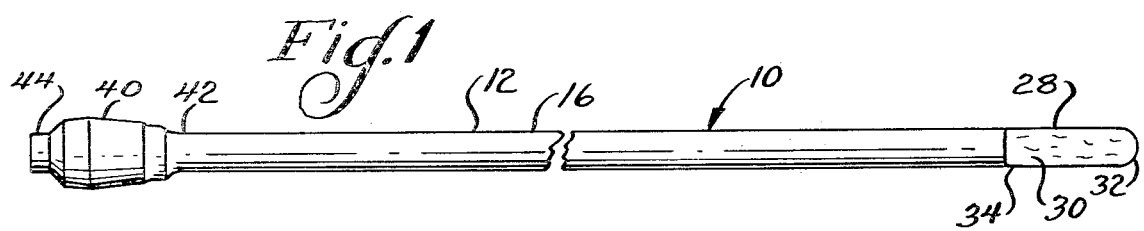
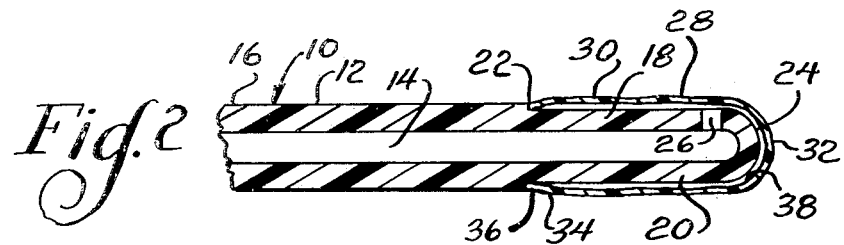
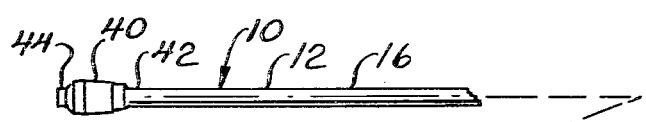
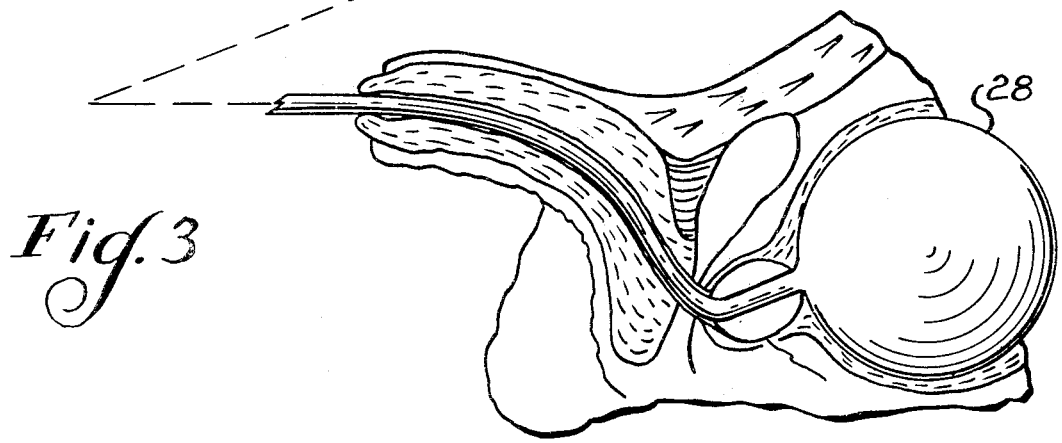
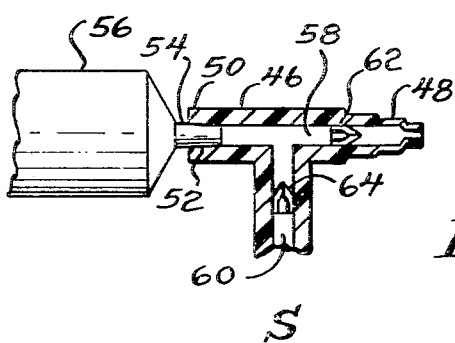

BLADDER HEMOSTATIC CATHETER

BACKGROUND OF THE INVENTION

The present invention relates to catheters, and more particularly to bladder hemostatic catheters.

Subsequent to surgery in the bladder of a patient, a condition of excessive bleeding may persist, thus posing possible danger to the patient unless the bleeding is stopped. In the past, physicians have injected formaldehyde into the bladder during attempts to terminate such hemorrhages, but such a procedure may result in damage to the cell lining of the bladder. Alternatively, in the absence of a better procedure, the physician may be required to perform further surgery in order to again suture the wound. Of course, such additional surgery is undesirable when it is not absolutely required.

SUMMARY OF THE INVENTION

A principal feature of the present invention is the provision of an improved bladder hemostatic catheter of simplified construction.

The hemostatic catheter of the present invention comprises, an elongated shaft having a lumen extending along the shaft, a central section of a first outer diameter, an annular end section at the distal end of the shaft having a second outer diameter less than the first diameter of the central section, with the end section defining a tip of the shaft, and an opening in the end section communicating between the lumen and the outside of the shaft. The catheter has an inflatable ballon of elastic material covering the end section of the shaft, with the ballon having an annular segment and a closed distal end extending around the tip, and with a proximal end of the segment being bonded to the shaft in a circumferential zone adjacent the juncture of the central and end sections of the shaft. The ballon defines a cavity intermediate the balloon and end section of the shaft communicating with the opening, and with the remainder of the shaft proximal the balloon being closed. The catheter has valve means connected to a proximal end of the shaft and communicating with the lumen, with the valve means controlling passage of fluid for inflation and deflation of the balloon. The catheter may also have a syringe for pumping fluid, and a valve assembly for connection to the pumping means, a source of fluid, and the catheter lumen through the valve means.

A feature of the present invention is that the balloon is capable of receiving 600 to 1000 cubic centimeters of fluid when inflated.

Still another feature of the invention is that the balloon assumes a generally spherical shape in the inflated state of the balloon.

Thus, a feature of the present invention is that the inflated ballon substantially fills the bladder and applies pressure to the bladder walls in order to stop bleeding.

Yet another feature of the invention is that the valve means permits inflation and deflation of the balloon in a simplified manner.

A further feature of the present invention is that the valve assembly permits passage of fluid from the source to the syringe while preventing passage of fluid from the syringe to the source, and the valve assembly permits passage of fluid from the syringe to the lumen while preventing passage of fluid from the lumen to the syringe.

Thus, another feature of the invention is that the valve assembly permits inflation of the balloon with a substantial volume of the fluid during continuous pumping of the syringe in a simplified manner.

Further features will become more fully apparent in the following description of the embodiments of this invention and from the appended claims.

DESCRIPTION OF THE DRAWINGS

In the drawings:

FIG. 1 is a fragmentary elevational view of a bladder hemostatic catheter of the present invention;

FIG. 2 is a fragmentary sectional view of a distal end of the catheter of FIG. 1;

FIG. 3 is a fragmentary elevational view of the catheter of FIG. 1 illustrating a balloon of the catheter in an inflated configuration; and FIG. 4 is a fragmentary elevational view, taken partly in section, illustrating a valve assembly for use in the catheter to facilitate inflation of the catheter balloon.

DESCRIPTION OF THE PREFERRED EMBODIMENTS

Referring now to FIGS. 1 and 2, there is shown a bladder hemostatic catheter generally designated 10 having an elongated shaft 12 defining a lumen 14 extending through the shaft. The shaft 12 has an elongated central section 16 having a first outer diameter, and an annular end section 18 at a distal end 20 of the shaft 12 having a second outer diameter less than the first diameter of the central section 16, with the end section 18 and central section 16 being connected at a circumferential shoulder 22, and with the end section 18 defining a tip 24 at the distal end 20 of the shaft 12. The shaft 12 also has an opening 26 adjacent the distal end 20 of the shaft 12, with the opening 26 communicating between the lumen 14 and the outside of the shaft 12.

The catheter 10 also has an inflatable balloon 28 of elastic material, such as rubber, covering the end section 18 of the shaft 12. The balloon has an annular segment 30 and a closed distal end 32 which extends around the shaft tip 24. A proximal end 34 of the balloon 28 is bonded to the shaft 12 in a circumferential zone by suitable means 36, such as adhesive, adjacent the location of the shaft shoulder 22. As shown, the uninflated balloon has an outside diameter approximately equal to the outside diameter of the central section 16 due to the recessed end section 18 in order to facilitate passage of the catheter through the patient's urethra during placement.

The balloon 28 defines a cavity 38 intermediate the balloon 28 and the shaft 12, with the cavity 38 communicating with the catheter lumen 14 through the opening 26 to permit inflation of the balloon. The balloon has an appropriate shape and sufficient elasticity in order to receive 600 to 1000 cubic centimeters of fluid, such as water or a saline solution, in the cavity 38 when the balloon is inflated, such that the balloon assumes an enlarged generally spherical configuration in inflated condition, as shown in FIG. 3.

With reference to FIGS. 1 and 3, the catheter 10 has a valve member 40 of known type secured to a proximal end 42 of the catheter shaft. The valve member 40 normally assumes a closed configuration, such that the valve member prevents passage of fluid between the catheter lumen 14 and the outside of the catheter. The valve member 40 opens responsive to contact by the tip of a syringe, or other suitable instrument, through a proximal end 44 of the valve member 40 in order to permit inflation and deflation of the balloon 28.

With reference to FIG. 4, the catheter has a valve assembly 46 having a distal end 48 for placement in and actuation of the valve member 40. The valve assembly 46 also has a proximal end 50 defining a port 52 to releasably receive the tip 54 of a syringe 56. The valve assembly 46 also has a first passageway 58 communicating between the port 52 and the distal end 48 of the valve assembly 46, and a second passageway 60 communicating between a source S of fluid and the first passageway 58. The valve assembly 46 has a first on-way valve element 62 located in the first passageway 58 at a position intermediate the juncture of the first and second passageways 58 and 60 and the distal end 48 of the valve assembly 46. The valve assembly 46 also has a second one-way valve element 64 located in the second passageway 60. The first and second valve elements 62 and 64 may be of any suitable type, such as flap valves, as shown. The first valve element 62 permits passage of fluid from the syringe tip 54 to the distal end 48 of the valve assembly, and prevents passage of fluid in the reverse direction. Similarly, the second valve element 64 permits passage of fluid from the source S to the first passageway 58 and the syringe 56, while preventing passage of fluid in the second passageway 60 in the reverse direction.

In use, the distal end 20 of the catheter 10 is passed through the urethra of the patient until the ballon 28 is located in the bladder. Next, the distal end 48 of the valve assembly 46 is placed in the proximal end 44 of the valve member 40 in order to actuate the valve member 40 and establish communication between the valve assembly 46 and the catheter lumen 14 through the valve member 40. The syringe tip 54 is placed in the port 52 at the proximal end 50 of the valve assembly 46, and the valve assembly 46 is connected to the fluid source S.

After the placement procedure has been completed, the syringe 56 is pumped in order to withdraw a quantity of fluid from the source S through the second valve element 64 into the syringe 56, and expel the fluid from the syringe 56 through the first valve element 62 into the catheter lumen 14 and the balloon 28. Due to the relatively large volume capacity of the balloon, the syringe must be repetitively pumped in order to eject a sufficient quantity of fluid into the balloon cavity 38, and inflate the balloon into the enlarged configuration substantially filling the bladder, as shown in FIG. 3, after which the valve assembly 46 is removed from the valve member 40.

In the inflated condition of the balloon, the balloon closes the bladder, and applies pressure to the bladder walls to stop bleeding in the bladder when a hemorrhage exists after surgery. In the usual case, it is expected that the balloon will be retained in the inflated configuration for approximately 15 to 20 minutes in order to accomplish hemostasis, although the procedure may last up to approximately 6 hours if necessary. Once a sufficient period of time has elapsed, the balloon may be deflated through actuation of the valve member 40 in order to open the valve member and permit passage of the fluid from the balloon to the outside of the catheter after which the catheter is removed from the patient.

The foregoing detailed description is given for clearness of understanding only, and not unnecessary limitations should be understood therefrom, as modifications will be obvious to those skilled in the art.

I claim:

1. A bladder hemostatic catheter, comprising:

an elongated shaft having only one lumen in the shaft, a central section of a first outer diameter, an annular end section at the distal end of the shaft having a second outer diameter less that the first diameter of said central section, with said end section defining a tip of the shaft, and an opening in said end section communicating between said lumen and the ouside of the shaft;

an inflatable balloon of elastic material covering said end section of the shaft, said balloon having an annular segment and a closed distal end extending around said tip, with a proximal end of said segment being bonded to the shaft in a circumferential zone adjacent the juncture of said central and end sections of the shaft, said balloon defining a closed cavity intermediate the balloon and end section of the shaft communicating with said opening, with the remainder of the shaft proximal said balloon being closed, and said balloon being capable of receiving 600 to 1000 cubic centimeters of fluid and assuming a generally spherical shape in an inflated state of the balloon; and valve means connected to a proximal end of the shaft and communicating with said lumen, said valve means controlling passage of fluid for inflation and deflation of said balloon, said valve means comprising a first known valve member which actuates responsive to contact by the tip of a syringe to permit passage of fluid through the valve means to said shaft lumen and closes responsive to withdrawal of the tip of a syringe, to prevent passage of fluid from said shaft lumen through said valve member, said valve means further comprising a valve assembly insertable into said valve member and having a first passageway communicating with the valve member, a second passageway communicating between said first passageway and a source of fluid, a first one-way valve element in the first passageway permitting passage of fluid from the second passage-way to the valve member and preventing passage of fluid from the valve member to the second passageway, and a second one-way valve element permitting passage of fluid from the source to the first passageway and preventing passage of fluid from the first passageway to the source, whereby upon completed inflation of said balloon through said valve means, said valve assembly may be withdrawn from said valve member and said balloon will remain inflated for a selected period of time, whereafter said valve member may be deflated through actuation of said valve member.

* * * * *